United States Patent [19]
Golovanivsky et al.

[11] Patent Number: 5,461,656
[45] Date of Patent: Oct. 24, 1995

[54] MICROWAVE X-RAY SOURCE AND METHODS OF STERILIZATION

[75] Inventors: Konstantin S. Golovanivsky, Grenoble, France; Valeri D. Dugar-Zhabon, Moscow, Russian Federation

[73] Assignee: Ruxam, Inc., New York, N.Y.

[21] Appl. No.: 237,177

[22] Filed: May 3, 1994

Related U.S. Application Data

[62] Division of Ser. No. 843,569, Feb. 28, 1992, Pat. No. 5,323,442.

[51] Int. Cl.$^6$ .................................................. G21K 5/08
[52] U.S. Cl. ................................................ 378/66; 378/64
[58] Field of Search .................................. 378/66, 67, 64

[56] References Cited

U.S. PATENT DOCUMENTS

3,767,918 10/1973 Graybeal .................................. 378/67

Primary Examiner—Craig E. Church
Attorney, Agent, or Firm—Davis Hoxie Faithfull & Hapgood

[57] ABSTRACT

An X-ray source that produces X-rays as a result of igniting an electron cyclotron resonance plasma inside a vacuumated dielectric spherical chamber filled with a heavy atomic weight, non-reactive gas or gas mixture at low pressure. The spherical chamber is located inside a non-vacuumated microwave resonant cavity that is in turn located between two magnets to form a magnetic mirror. Conventional microwave energy fed into the resonant cavity ignites the plasma and creates a hot electron ring which electrons bombard the heavy gas and dielectric material to create an X-ray emission. The X-ray source is suitable for surface and volume sterilization of foodstuffs, packaged goods, medical supplies, blood products and other materials and medical diagnostic and therapeutic devices such as tomography, mammography and radiology.

16 Claims, 5 Drawing Sheets

MICROWAVE X-RAY SOURCE AND METHODS OF STERILIZATION

This is a divisional of application Ser. No. 07/843,569 filed on Feb. 28, 1992, now U.S. Pat. No. 5,323,442.

FIELD OF THE INVENTION

The present invention concerns an X-ray source and method of surface and volume sterilization of such objects as seeds, foods, water, medical supplies and instruments, and numerous other items. More particularly, it concerns the use of an electron cyclotron resonance (ECR) plasma to provide such a source and method.

BACKGROUND OF THE INVENTION

The classical X-ray sources that have been used for sterilization are generally either radioactive nuclides or high voltage vacuum tubes, both of which have limited applications. The radioactive nuclides typically have comparatively short lives and are expensive and dangerous to handle. In addition, the gamma or X-ray intensity they produce cannot be readily monitored and, once activated, the sources cannot be turned off. The high voltage vacuum tube apparatus requires heavy and cumbersome high voltage supplies, which are also dangerous to handle. Further, this apparatus needs highly qualified personnel to operate and maintain it.

To avoid these deficiencies it was recently proposed to use a compact cyclic electron accelerator as a source of X-ray in the range of 150 keV photon energy. See H. R. Gardner, T. Ohkawa, A. M. Howald, A. W. Leonard, L. S. Peranich and J. R. D'Aoust, Rev. Sci. Instruments, 61(2), February 1990, pages 724–727. In this source, the electrons are injected from an electron emitter into a vacuumated resonant cavity, and accelerated by a microwave field along a spiral orbit to a molybdenum target, which produces the X-ray radiation. Although this source advantageously avoids the use of radioactive nuclides and a high voltage supply, it is not a reliable tool for routine use in the industry and agriculture. The reasons are that the emitted X-ray intensity is too weak, and the life of the device is limited by the life of an electron emitter, which cannot readily be replaced without the replacing of the entire vacuumated cavity. Also, since the X-rays are produced by an electron beam striking a molybdenum target, only half of the produced X-rays are reflected from the target, to be useful, while the other half are absorbed in the target and lost. Further, this source cannot produce homogeneous X-ray radiation in all radial directions from a central source, such as is useful, for example, in sterilizing fluids, e.g., water, from a source centrally located within the flow of the fluid as described below.

There remains a continuing need for better sources of X-rays, and in particular for economical X-ray sources having sufficient intensity for surface and volume sterilization of goods and food stuffs.

SUMMARY OF THE INVENTION

The present invention concerns an X-ray source which is free of the above deficiencies and provides nearly the same X-ray intensity and energy as the classical high voltage X-ray sources, although it has a drastically smaller volume, weight, electrical consumption and cost. In addition, the X-ray source of the present invention has no elements, such as microwave coupling elements, electron emitters, targets or the like, within a vacuumated volume. This dramatically increases the stability, reliability, intensity and life of the source. In addition, it does not rely on radioactive nuclides or a high voltage supply, and it is extremely reliable and simple both in operation and maintenance. Advantageously, because of its small size and low cost, the X-ray source of the present invention can be used in small scale operations such as local food processing plants and the like, unlike the known commercial devices which are limited to large sterilization plants. The present invention also concerns using multiple X-ray sources, cascaded in succession along an existing processing or packaging line or assembled in modular units to achieve whatever cumulative amount of X-ray radiation may be desired for a given throughput rate. Moreover, the X-ray sources can be made mobile and easily transported to any location for use.

Broadly, the invention is directed to apparatus and methods for producing X-ray radiation by providing a vacuumated chamber that is made of a dielectric material and is filled with a heavy atomic weight gas at low pressure and placing the chamber in a resonant magnetic field that generates an Electron Cyclotron Resonance (ECR) plasma inside the chamber. The hot electrons of the ECR plasma bombard the heavy gas in the chamber and the dielectric material of the chamber which in turn produces X-ray radiation. The vacuumated chamber is preferably a spherical quartz glass chamber and the heavy gas is preferably xenon gas.

In one embodiment, the ECR plasma is generated by placing the chamber inside a non-vacuumated microwave resonant cavity which is in its turn disposed in a magnetic field, preferably between opposite poles of two permanent magnets. This configuration, when microwave energy is coupled into the resonant cavity, provides a compact axisymmetric magnetic mirror configuration with an ECR plasma inside of the chamber with respect of the selected microwave frequency. This is described in greater detail below. The resultant X-ray is emitted homogeneously in the equatorial plane of the cavity perpendicular to the magnetic field axis.

The lateral wall of the resonant cavity is made of a material which is transparent for the X-ray, but is not transparent for the microwave. For example, a light metal, e.g., aluminum, grid having an appropriate mesh size for trapping microwaves is preferred. The electrical (microwave) supply required for this X-ray source (which is referred below as ECR-X) is similar to those of conventional domestic microwave ovens, but it consumes only half of the electrical power (~1 kW).

Another aspect of the invention concerns a method of forming a source for use in producing X-rays, which source is a replaceable item of an apparatus for producing X-rays. One method of forming such a source includes the steps of:

forming a chamber of a dielectric material;

evacuating the chamber under conditions of temperature and pressure sufficient to out gas impurities from the dielectric material;

filling the chamber with a heavy atomic weight gas or gas mixture; and sealing the chamber with the pressure inside the chamber being between $10^{-4}$ and $10^{-5}$ Torr.

Another aspect of the present invention concerns apparatus for irradiating a material, article, or product that is being processed or conveyed with X-ray radiation. One such apparatus includes:

a plurality of X-ray sources, each X-ray source comprising:

a microwave resonant cavity;

a sealed vacuumated chamber filled with a heavy atomic weight gas or gas mixture located inside the cavity; and means for applying a magnetic field to the sealed chamber for use in producing an electron cyclotron resonance plasma within the chamber; and means for advancing the material to be exposed to X-rays emitted by one or more of the plurality of X-ray sources.

A cladding, surrounding the advancing means and plurality of X-ray sources, is preferably provided for containing X-rays. The cladding is provided with one or more openings for the entry and exit of materials.

Preferably, the apparatus includes a source of microwave energy, which may be one supply or more than one supply, and a waveguide network for feeding microwaves from the source to the resonant cavity of each of the X-ray sources. The waveguide network may be configured so that each microwave energy source feeds microwaves to more than one X-ray source.

The apparatus further may be built on a movable platform, such as a truck, a trailer attachable to a vehicle, an airplane or other movable structure. The term "truck bed" refers to a platform on a truck or other automotive vehicle or a trailer attachable to another automotive vehicle.

Another aspect of the invention concerns a method for sterilizing water or other flowing material comprising:

(a) forming a flow passageway for passing the water or other material through a defined area;

(b) providing a non radioactive source for producing X-rays inside the flow passageway;

(c) generating X-rays inside the flow passageway at a first intensity;

(d) passing the material in a flow at a first rate through the flow passageway and the X-rays to sterilize the water or other material.

Preferably, the passageway is clad with a material for containing X-rays. They may be more than one non radioactive X-ray source, each source being interposed in the flowpath and spaced apart along the passageway and generating X-rays at an intensity so that the flowing material is cumulatively exposed to an intensity that corresponds to the first intensity. Preferably, each source is an ECR-X source immersed in the flow. Also, the flow passageway may be bent on opposite sides of the X-ray source(s) and cladding applied to the flow passageway between and about the bends so that X-rays generated by the source(s) inside the flow passageway are confined within the flow passageway.

BRIEF DESCRIPTION OF THE FIGURES

Further features of the invention, its nature and various advantages will be more apparent from the drawings and the following detailed description of the invention, in which like reference numerals refer to like elements, and in which.

DETAILED DESCRIPTION OF THE INVENTION

Figure 1:
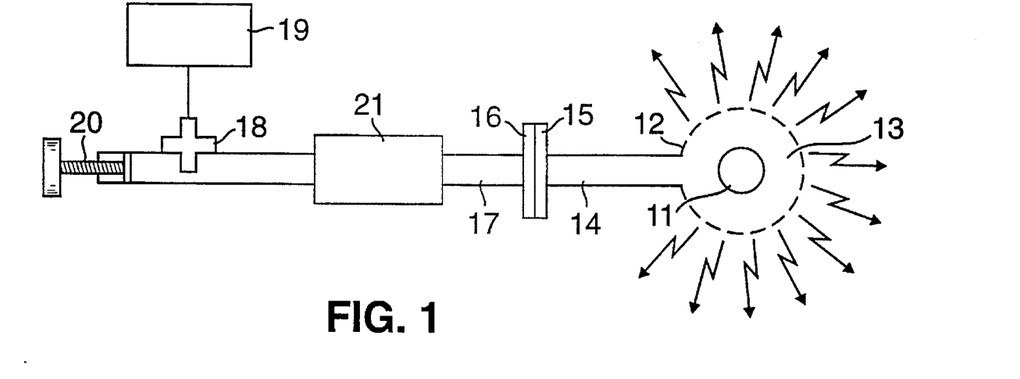
FIG. 1 shows a schematic view of the overall ECR-X source of the present invention.
Figure 2:
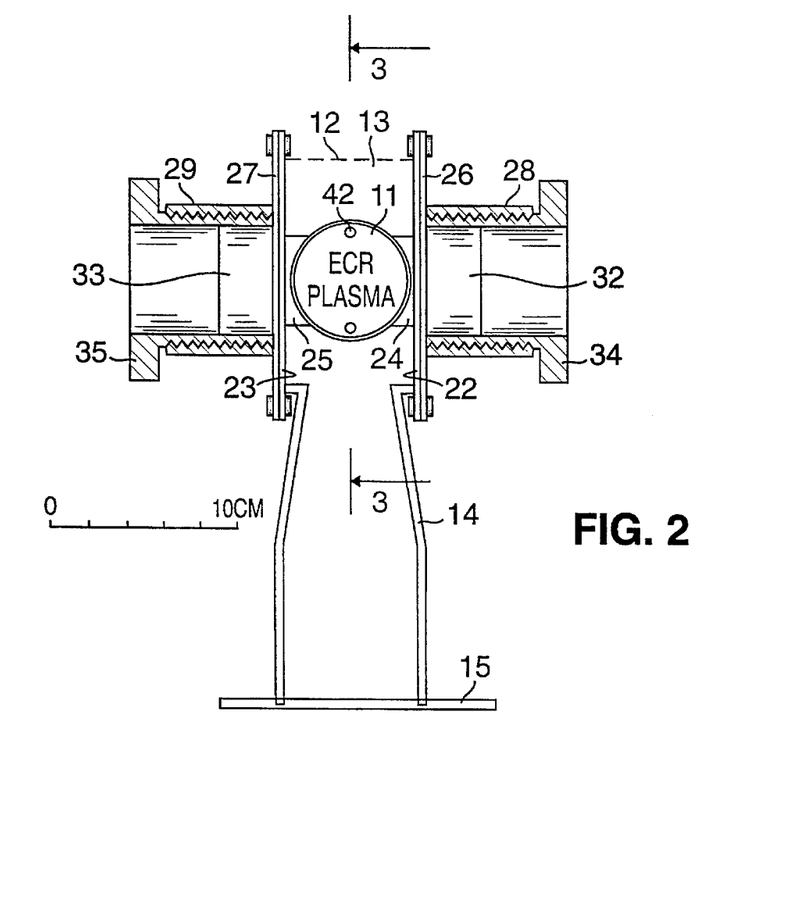
FIG. 2 shows the detailed construction of the radiating block used in FIG. 1, drawn to the scale illustrated in FIG. 2.
Figure 3:
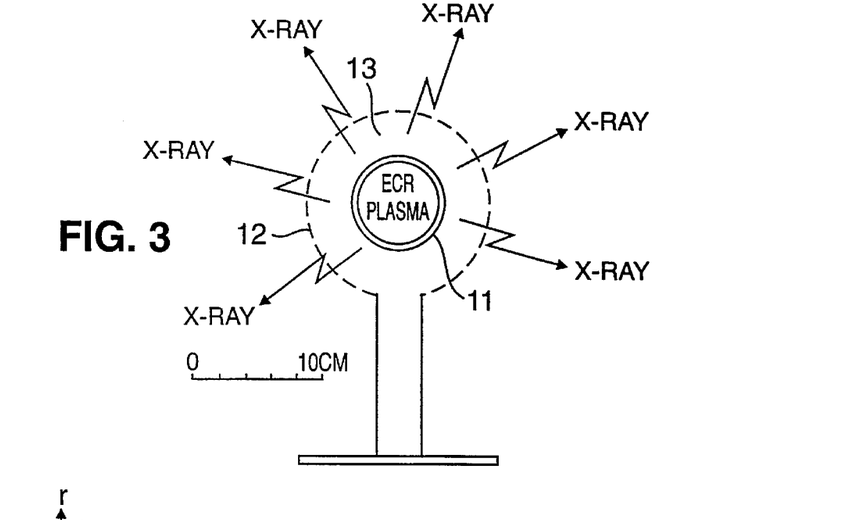
FIG. 3 shows a schematic view of the radiating sphere inside a resonant cavity, drawn to the illustrated scale, as it appears in a section taken along a center-line through FIG. 2.

Referring to FIGS. 1 to 3, there are four basic components in the preferred embodiment of the ECR-X source 10 of the present invention, namely, a spherical chamber 11 filled by a heavy gas at a low pressure, a cylindrical grid 12 that surrounds the chamber 11 and forms a resonant microwave cavity 13, a microwave power source 18, and a magnetic mirror formed by magnets 32 and 33, which is effective within sphere 11, as will be explained. The microwave source and magnets combine to form an electron cyclotron resonance (ECR) plasma within the sphere 11, as will also be explained.

The actual source of the X-ray radiation is the small dielectric sphere 11 filled with a heavy non-reactive gas. The sphere 11 is about the size of a tennis ball, as indicated by the scale shown in FIGS. 2 and 3. This dielectric sphere is preferably made of quartz, but it may be glass or ceramic or other material that will not react with the heavy gas. The gas is preferably xenon, but it also can be krypton or argon, or any other inert gas. Further, the gas can be a heavy non-inert gas, so long as the gas is non-active in relation to the surrounding sphere, or a mixture of gases.

A heavy gas is desired so that it will line the inside surface of chamber 11, absorb a substantial portion of the electrons from a hot electron ring, to be discussed, and emit X-ray energy. Further, the penetration of the atoms of the heavy gas into the dielectric wall of sphere 11 is negligible so that the gas pressure in chamber 11 remains constant during practically unlimited time. In addition, the start-up of a plasma is very easy in heavy gases as compared to light gases due to the smaller mobility of the heavy ions. Also the electron density reached in the heavy gas plasma is higher than in light gases at the same microwave power, because of the reduced losses due to the low mobility of the heavy ions.

The sphere 11 is filled with the heavy gas in a well-known manner, for example, by evacuating the sphere on a commercially available vacuum pump, at an elevated temperature, to out gas any impurities in the quartz or other material of the sphere, in order to ensure prolonged life of the sphere as an X-ray source. Once evacuated and processed to remove impurities, the sphere is filled with the heavy gas, and the tubulation used for out-gassing and filling is sealed.

In the preferred embodiment, the X-ray source apparatus includes a non-vacuumated cylindrical resonant cavity 13 which resonates in the $TE_{111}$ mode. Cavities that resonate in other modes that have the electrical field component perpendicular to the static magnetic field axis also may be used. Cavity 13 is preferably formed of a grid 12, preferably made of beryllium or aluminum. The cavity 13 is about 1 liter in volume and it encompasses the closed spherical dielectric chamber 11.

Microwave power is passed into cavity 13 through the waveguide 14, which is connected through the flanges 15 and 16 with the waveguide 17 that supplies microwave energy from an oscillator 18, which may be a magnetron fed from an electrical supply 19. The microwave energy from oscillator 18 is preferably at a frequency of 2.45 GHz. The coupling between the magnetron 18 and the waveguide is conventionally optimized by means of a movable plunger 20 which may be mounted on a slide or threads for adjusting its position. The magnetron is protected against any reflected microwave energy by a conventional circulator device 21.

FIGS. 2 and 3 show the construction of the X-ray radiating block in some detail. As shown in these figures, the resonant cavity is composed of a cylindrical lateral wall 12 and two flanges 22 and 23. The cylindrical wall 12 is made of a grid of light metal, such as beryllium or aluminum. The grid 12 contains the microwave energy employed, at 2.45 GHz, but is transparent to the X-rays emitted from sphere 11. If necessary, the base material of the grid 12, such as beryllium or aluminum, is preferably coated with a thin coating of high electrical conductivity material, such as copper, to minimize its heating. The coating can be about 10 micrometers thick. Moreover, air cooling (ambient or forced) of the grid 12 and resonant cavity 13 is advantageously employed to provide the quartz chamber cooling.

Grid 12 is attached to a rectangular waveguide section 14 which is connected with the microwave supply 18 through the flange 15. The cylindrical wall 12 is fixed between the two flanges 22 and 23, which can be made of duraluminum or copper, and two dielectric cushions 24 and 25 which serve to support the spherical plasma chamber 11 within the resonant cavity. These dielectric cushions are preferably porous teflon, and they may be mechanically attached to flanges 22 and 23. Alternatively, the cushions may be a foam material or any other cushioning dielectric non-magnetic material that can be appropriately shaped and secured to support sphere 11 in place without absorbing microwave energy.

The cylindrical wall 12 and two flanges 22 and 23, once being assembled in the apparatus of FIGS. 1 to 3, form a resonant cavity for the microwave energy at 2.45 GHz. This cavity is fed microwave energy from source 18 through the circulator 21, and waveguide sections 17 and 14, waveguide 14 being tightly connected to the flanges 22 and 23 to minimize any losses. Wave guides 14 and 17 are standard units of copper or aluminum.

As shown in FIG. 2, flanges 26 and 27 are attached by bolts to flanges 22 and 23. A braided copper seal can be inserted between flanges 22 and 26, and between flanges 23 and 27, to be compressed when the bolts attaching the flanges are drawn together, to avoid any microwave energy leakage. Flanges 26 and 27 include cylindrical tubes 28 and 29, which are internally threaded. As shown in FIG. 2, the apparatus also includes two disk-shaped permanent magnets 32 and 33, which are preferably $SmCo_5$, fixed in casings 34 and 35. These casings and tubes 28 and 29 have a common thread, so that the casings can be screw threaded with the tubes, and thereby adjust the position of magnets 32 and 33 by rotating the casings.

The only element of the apparatus that must be occasionally replaced is the sphere 11, which has a nominal useful life of about 1000 hours of operation as the plasma chamber. The cost of this sphere can be quite low, and the replacement operation does not require any special skill. In this regard, the sphere 11 is removably mounted in the cavity 13. To replace the spherical chamber 11, one need only separate one of the flanges 26 or 27, replace the old chamber 11 by a new one, preferably leaving dielectric cushions 24 and 25 in place (unless their replacement is appropriate), and then re-attach the flange. This operation can be done in a short time.

To start the ECR-X source, one starts the microwave oscillator 18. This transmits microwave energy at a frequency of 2.45 GHz through the waveguide to the resonant cavity 13. Since the magnets 32 and 33 are in place, the presence of the microwave energy in the chamber 11 causes the ECR plasma to form and the X-ray emission to begin. The X-ray emission is a bremsstrahlung with the peak energy between 100 and 200 keV depending on the microwave power applied, e.g., from 200 to 500 watts. To stop the X-ray emission, one simply turns off the microwave oscillator. This is adequate for many sterilization or preservation methods as disclosed herein.

The effectiveness of any X-ray source to sterilize and preserve food and other materials is a function of the amount of X-ray energy and the time of exposure. According to the present invention, a method of sterilizing an article, a product or materials, in a rapidly moving processing line or the like can be achieved by placing the X-ray sources shown in FIGS. 1 to 3 one after another along the line so that each article or product and all the material advancing along the line receives a cumulative X-ray dose sufficient to cause sterilization. Also, the ECR chambers of successive sources can be offset from one another, so as to irradiate the article or product from different angles.

The food products and other items to be sterilized or preserved using the foregoing X-ray source can be unwrapped or wrapped. It can, for example, include products wrapped in plastic foil, wine in bottles, sterile gauze in a carton, and other covered items, provided that the wrapping is transparent to the X-ray.

An understanding of the operation of the ECR plasma in the sphere 11, and additional insight into the mode of operation of the X-ray source, can be gleaned with reference to FIGS. 4 to 7 and the following discussion.

Figure 4A:
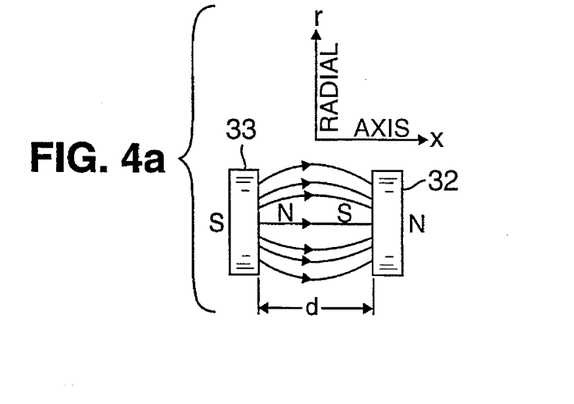
FIGS. 4a–4c and 5 through 7 show magnetic field lines, field strength and other parameters that are useful in understanding the apparatus shown in FIGS. 1 to 3.
Figure 4B:
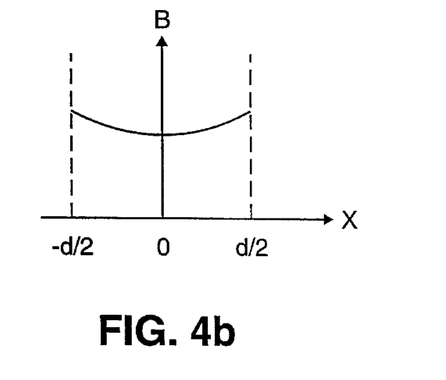

The disk-shaped magnets 32 and 33 in FIG. 2, are shown in FIG. 4(a) with an illustration of the magnetic field lines they produce. Also, the axial and radial directions are depicted. As shown by the closeness of the field lines, the magnetic field increases as one moves from the center of the magnetic field toward either of the magnets, as shown by the graph in FIG. 4(b). Also, it decreases as one moves from the center of the field in a radial direction, as shown by the graph in FIG. 4(c).

Figure 5:
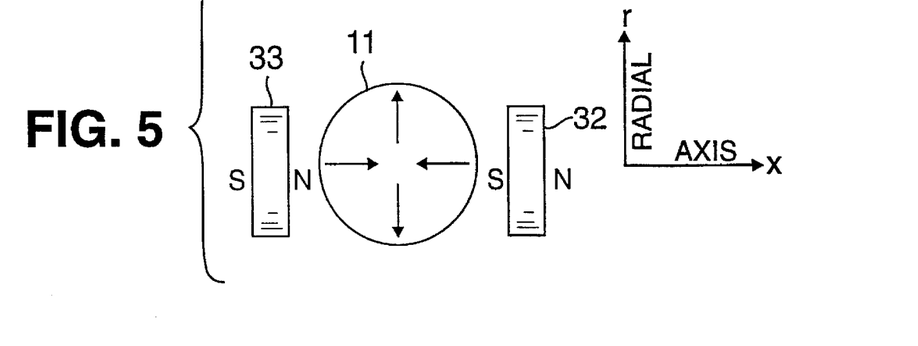

In FIG. 5, the arrows within the plasma chamber 11 show the direction of the forces on the plasma particles, which are produced by the magnetic field, to create a well-known magnetic mirror.

Figure 4C:
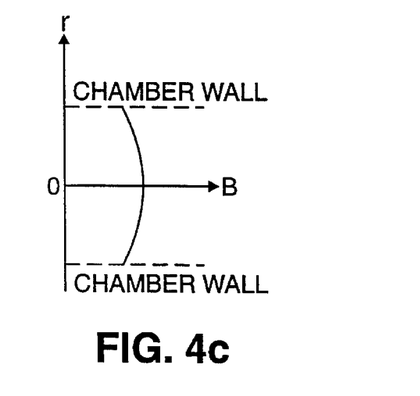

For microwave energy at 2.45 GHz, electron cyclotron resonance (ECR) occurs for a magnetic field strength of 865 gauss. The magnets 32 and 33, and their spacing, are chosen, and adjusted in position, so that the magnetic field strength along the axis between the magnets, as shown in FIG. 4(a), is higher than 865 gauss. This also is true for the field strength at the center of the magnetic field moving in a radial direction. However, as shown in FIG. 4(c), as one nears the spherical chamber wall the magnetic field decreases.

Figure 6:
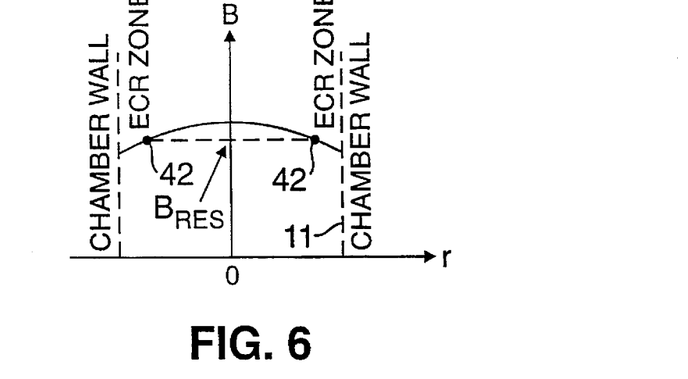

Thus, near the internal surface of the sphere 11, along the centerline between magnets 32 and 33, a point will be reached where ECR resonance occurs, as shown in FIG. 6. This produces an equatorial ring 42 of hot electrons, which has been observed as an associated effect in some past ECR work. See W. D. Dougar-Jabon, K. S. Golovanivsky and V. D. Schepilov, "Accumulation of Multicharged Ions in Plasma with Electrostatic Well Induced by ECR", *Physica Scripta (Sweden)*, Vol. 18, 506–507, 1978.

Figure 7:
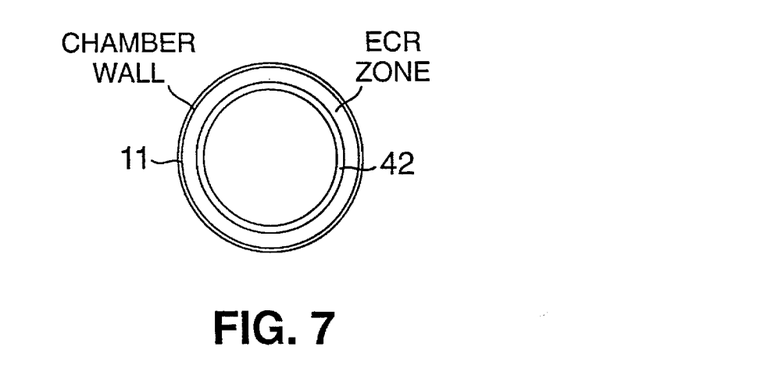

The hot electron ring 42 also is shown in FIGS. 2, 3 and 7. In the operation of sphere 11, electrons in the hot electron ring spiral off from the ring due to the so-called flute instability, which is a well known physical phenomenon. These spiraling electrons collide with a dense layer of atoms of the gas within sphere 11, and with the internal surface of the sphere. As a consequence, X-rays are emitted in a divergent array, from the heavy gas particles and the material of the sphere 11, along an equatorial region about sphere 11, as shown in FIGS. 1 and 2.

With the magnets 32 and 33 properly positioned, the hot electron ring or an ECR zone 42 will be circular and symmetrical within the sphere 11, and the X-ray emission will consequently be homogeneous along the equatorial region. By a proper adjustment of the magnets, the ECR zone can be properly placed, in proximity to the sphere wall, to achieve the optimum X-ray emission.

Any X-rays passing back through waveguide 14 will diminish in strength with distance, and the divergent nature of the X-rays will cause them to be absorbed by the copper waveguide 14. Also, the waveguide 17 can include a turn to ensure that no X-rays will reach the region of oscillator 18. Alternatively, a waveguide turn can occur just outside one of the cylinders 28 and 29, without disrupting grid 12, so that grid 12 can extend the entire 360° around the ECR plasma in sphere 11. In this fashion, the X-ray radiation can be emitted radially over 360°.

While chamber 11 has been described as a sphere, it can also be ellipsoid in shape. Other shapes, such as a cube, can also be used for chamber 11, so long as the chamber has enough physical strength to withstand the external pressure, but a sphere is preferable both because of its strength and symmetrical shape.

Some of the parameters that are believed to be particularly advantageous are that the microwave resonant cavity 13 has a volume of about 1 liter, height of about 7 cm. and a diameter of 13 cm. The microwave energy is desirably at 300 to 500 watts at the stated frequency of 2.45 GHz. The ECR chamber 11 has a volume preferably about 100 $cm^3$, and it is about 6 cm. in diameter, made of quartz glass, with a wall thickness of 1.0 to 1.5 mm. Also, the gas within the ECR chamber 11 is preferably xenon, at an internal pressure of $10^{-5}$ to $10^{-4}$ Torr, preferably 3 to $8 \times 10^{-5}$ Torr, and more preferably 6 to $7 \times 10^{-5}$ Torr. The X-ray peak energy is around 180 keV, with an integral intensity of around 1 watt. Further, the grid 12 is preferably duraluminum, with a thin coating of copper that is about 10 micrometers thick. The dielectric cushions 24 and 25 are preferably porous teflon, and the magnets 32 and 33 are $SmCo_5$ disks, each having a height of about 2.5 cm., a diameter of about 5.5 cm., and a magnetic induction on the surface of about 0.4 Tesla. The magnetic field in the region of the hot electron ring is 865 gauss. The hot electron energy in the ECR plasma in sphere 11 is generally 150 to 250 keV, and the hot electron density is $2 \times 10^9$ per $cm^3$. The ring plasma volume is 3 $cm^3$; the plasma lifetime is 5 microseconds; the hot electron current is about 0.2 milliamps; and the energy delivered to the wall by the hot electrons is about 40 watts.

The source weighs about 20 kgs. and absorbs about 1 kW of electrical power.

If X-ray emission is desired in only a window along the equatorial line of emission, a cylinder of lead can be employed, surrounding the grid 12, to cover the height over which the X-ray emission extends, leaving an opening over the area of the desired window of emission. The window may have a desired shape, e.g., a point source hole, a slit, a rectangle, an annular configuration, etc. Lead having a thickness of 5 mm will suffice. One set of operable dimensions for the grid 12 is to have solid members that are about 1 mm in width or diameter separated by spaces that are about 5 mm.

Figure 8:
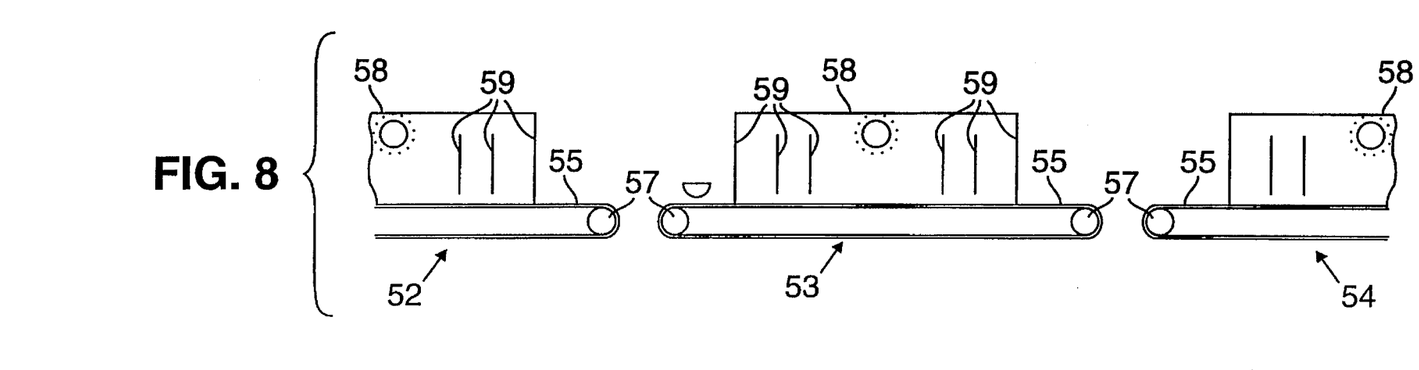
FIGS. 8 through 11 show some of the methods in which the X-ray source of FIGS. 1 to 3 can be employed, FIG. 11 being drawn to the illustrated scale.

FIGS. 8 to 11 illustrate various methods of radiating an article (or a product), a stream of articles, or a flow of a material with X-rays, for example, for sterilization or preservation. FIG. 8 shows a series of conveyors, each of which includes a belt 55 and a pair of rollers 57. Tunnels 58 are supported such that the conveyor belt 55 passes through or just below the tunnel, each tunnel having a series of lead or lead rubber curtains 59 of at least 3 mm, more preferably at least 5 mm, thickness. Also, an ECR plasma sphere 11, and the associated elements in FIGS. 1 to 3, are contained in each of the tunnels. An article or material to be sterilized or preserved will pass along the successive conveyors. As it meets a tunnel a first curtain will be pushed aside by the article, or automatically withdrawn as the article is sensed, by a photodetector or microswitch or the like. Successive curtains are preferably spaced so that the first curtain will close before the second curtain is opened. Once the article passes the last input curtain 59, it will be radiated as it continues along the conveyor, and then pass through the successive output curtains. By opening and closing the curtains in succession, no X-ray radiation will escape out of the ends of the tunnel.

Figure 9:
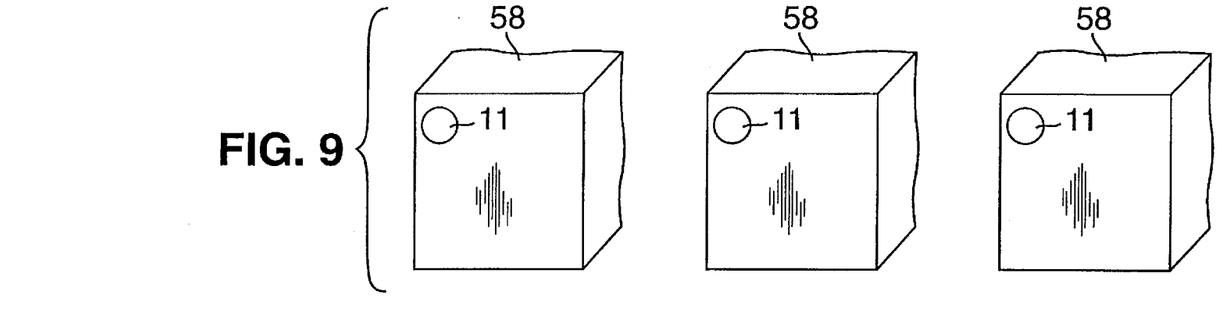

Alternatively, a single tunnel can include a series of ECR X-ray plasma sources and, as shown in FIG. 9, successive ones of the sources can be offset in order to radiate different portions of the article. By passing articles to be sterilized along the conveyors in FIG. 8, through one or more of the tunnels in FIGS. 8 and 9, the bacteria on the articles can be killed and the articles thereby sterilized. This method of irradiating an article with X-rays can be used for such articles as fruit or vegetables, chicken that may contain salmonella, shell fish or other foods, even wine in bottles, or wrapped meats. Also, it can be used for seeds that are to be used in foods, such as caraway seeds, and seeds that are to be planted. Further, it can be used for medical instruments and supplies, whether loose or packaged.

The present invention also concerns a method for irradiating articles or materials such as whole blood and cellular blood components, for example, to inactivate lymphocytes and some viruses at dosages that are not harmful to the viability of other desired blood cell components. And it can be used for irradiating waste products which may contain blood, viruses, bacteria or other organisms that present a risk of spreading disease or infection if disposed without treatment, such as food processing by-products (e.g., raw chicken scraps), used or disposable medical devices, instruments, supplies and blood contaminated materials, and medical diagnostic test by-products (e.g., blood samples, fluids and cultures).

The method of radiating fruits and other foods with X-rays according to the present invention eliminates the bacteria that causes the food to rot which acts to preserve the foods. Thus, the food can safely be shipped long distances, even over slow (and less expensive) travel routes. Further, fruits and other food can be allowed to ripen on the vines or in the orchards, so as to obtain a mature taste and appearance, as well as food value, and then sterilized locally, using the X-ray source and methods of the present invention, before being shipped to distant markets.

Moreover, since the X-ray source and methods of the present invention can operate on loose or packaged products, the X-ray source can be located in a processing or packaging plant either upstream or downstream of the processing or packaging stations.

The sterilization caused by radiation at doses established by the U.S. Food and Drug Administration may not remove all bacteria, and therefore foods may still require refrigeration, but it materially reduces the level of bacteria present and will prolong shelf life. For treatment of products where human or animal consumption of irradiated products is not a concern, the sterilization dosage may be sufficiently high to kill all undesired bacteria, viruses or other organisms.

Figure 10:
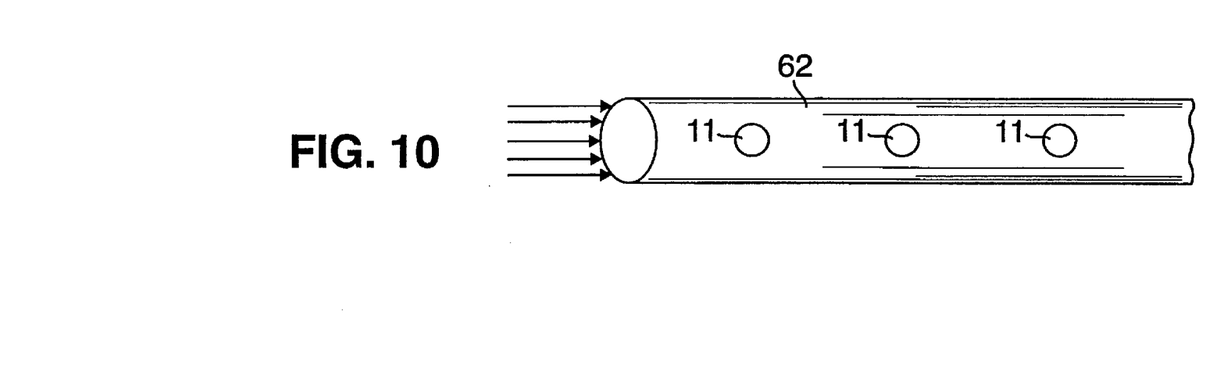

FIG. 10 shows a water supply pipe 62, which contains a series of centrally located ECR plasma sources 11, each with its associated elements shown in FIGS. 1 to 3. By passing the water along pipe 62, past the successive ECR plasma channels 11, the bacteria in a water supply can be killed and the water supply thereby sterilized. A similar process could be used for any fluid material flow, whether a gas, liquid or solid (solid, gel or particulate matter) flow.

It is noted that the method of sterilizing water using the non radioactive X-ray source immersed in the flow according to the present invention does not present the potential hazard of contaminating the entire water supply, which hazard would exist if a radioactive X-ray source were to be used for such purposes.

Figure 11:
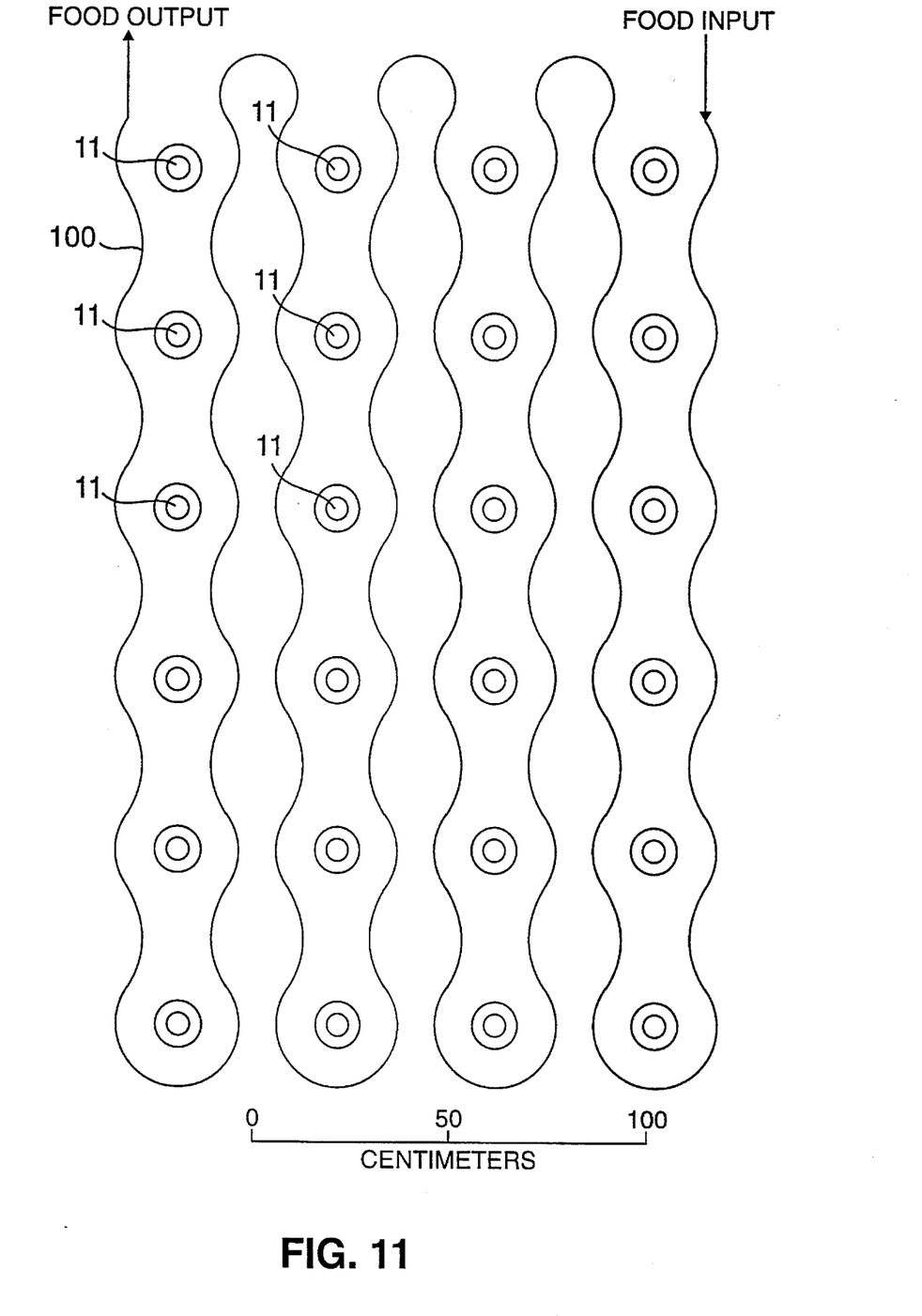

FIG. 11 shows a representation of a small scale sterilization station which includes a total of 24 ECR-X sources 11 arranged in a 4×6 matrix and a conveyor 100 for advancing articles along a path by and between the ECR-X sources. In this embodiment, each pair of a block of six ECR-X sources are coupled by a conventional microwave waveguide to a single microwave magnetron power supply, for example, a 12 kw c.w. commercial supply (not shown). Thus, only two such magnetrons are needed. The conveyor 100 is shown as having a tortuous path which is selected to maximize the dose of X-ray radiated from all directions on the articles being treated. Other paths, as well as more or lees ECR-X sources, could be used. The walls surrounding the track, and top and bottom of the station may be sealed to trap the X-rays by an appropriate material, e.g., lead lined walls and the aforementioned curtains for passing articles into and out of the station.

One suitable conveyor 100 is a single chain having hooks from which the articles may be suspended spaced apart, singly or in bulk containers or bundles, as appropriate. Preferably, the articles travel in a common equatorial plane of the ECR-X sources. Where necessary, the ECR-X sources may be arranged with equatorial planes that are offset horizontally, angularly, vertically or some combination thereof, to provide an adequate cumulative dose to the articles being treated.

Advantageously, the microwave magnetron sources may be driven by the same motor that operates the conveyor track. For example, a 100 kw gasoline-powered motor typical for operating a conveyor track can be used to produce 25 kw to operate the two magnetrons of this embodiment and to drive the chain conveyor. Such a facility can be constructed in any location where gasoline (or similar fuel source) can be obtained.

If the conveyor path has a length of 25 meters and is advanced at a speed of 1 cm/sec, then the X-ray dose provided is on the order of 2.5 kgy and the yield is on the order of 1 kgy per ten seconds. The faster the conveyor speed the lower the cumulative dose. Thus, the operating parameters can be selected to provide the following yields for the identified products: pork 5 kg per 10 seconds; fresh fruit 2.5 kg per 10 seconds; white potatoes 25 kg per 10 seconds; and poultry 1 kg per 10 seconds.

Advantageously, the entire station, composed of one or several blocks of 24 sources, can be installed on the bed of a large truck or trailer with a 100 kW motor and driven from location to location, for example, for processing grains, fruits and vegetables during harvesting in any location and environment. Either the truck bed may be sealed against X-ray leakage, or the bed may be parked inside a structure that can be sealed to trap X-rays.

It should be understood that the ECR-X source and methods of the present invention also could be used to irradiate articles, products and materials in a batch mode, wherein the X-rays are generated within a X-ray shielded structure and the structure has a platform for supporting the articles to be irradiated and a door (or similar opening) for inserting and removing articles such that the door has appropriate seals against X-ray leakage and interlocks for preventing X-ray generation when the door is open. Door seals could include, e.g., braided wire contact seals, X-ray absorbing dielectric seals, and/or waveguide chokes. The interlock system used may be a dual interlock of the type used in conventional domestic microwave ovens.

Another aspect of the invention is directed to a source and a method for irradiating body tissue with X-rays at a dosage level and for a time sufficient to medical or dental diagnostic or therapeutic purposes. Such methods include generating an ECR plasma to produce X-rays in a given direction, for example, to expose a film for X-ray evaluation of tissue, bone and other structures, including mammography and computer aided tomography (CAT scans). Such methods also include generating an ECR plasma to produce X-rays for medical therapeutics, for example, cancer therapy, diathermy, and activating X-ray responsive drugs. In this regard, the X-ray dosages to be used are those generally used in medical and dental diagnostic and therapeutic practices. Advantageously, the small and light weight of the ECR-X source, together with a lead shield that covers all of the cavity except a suitably shaped window, provide easy maneuverability to locate the source proximate to the patient and easy portability of the apparatus, for example, for a mobile medical clinic. In addition, the small size and simplicity of operation permits providing emergency service vehicles such as ambulances, fire rescue vehicles and the like with portable X-ray machines, which may be hand held, for obtaining X-ray images of injured patients prior to moving them.

One skilled in the art will appreciate that the present invention can be practiced by other than the described embodiments which are presented for purposes of illustration and not of limitation.

We claim:

1. A method for sterilizing water comprising:

(a) forming a flow passageway for passing water through a defined area;

(b) providing a non radioactive source for producing X-rays inside the flow passageway;

(c) generating X-rays inside the flow passageway at a first intensity;

(d) passing water through the flow passageway and the X-rays at a first rate sufficient to sterilize the water.

2. The method as in claim 1 further comprising:

(e) cladding the flow passageway with a material for containing X-rays.

3. The method as in claim 1 wherein step (b) further comprises providing an X-ray source having a vacuumated dielectric chamber containing a gas that produces an ECR plasma in an applied resonant magnetic field.

4. The method as in claim 1 wherein step (b) further comprises providing an ECR-X source.

5. The method as in claim 1 wherein step (b) further comprises providing more than one non radioactive X-ray source spaced apart, each source having a vacuumated dielectric chamber containing a gas that produces an ECR plasma in an applied resonant magnetic field and generating X-rays at an intensity so that the water flowing at a second rate is cumulatively exposed to X-rays sufficient to sterilize the water.

6. The method as in claim 5 wherein each non radioactive X-ray source is an ECR-X source.

7. The method as in claim 1 wherein steps (a) and (b) further comprise bending the flow passageway on opposite sides of the X-ray source and cladding the flow passageway between and about the bends with a material for containing X-rays so that X-rays generated by the source inside the flow passageway are confined within the flow passageway.

8. The method as in claims 3, 4, 5 or 6 wherein step (c) further comprises energizing each X-ray source with from 200 to 500 watts of microwave power.

9. A method for sterilizing a flowable material comprising:
   (a) forming a flow passageway for passing the material through a defined area;
   (b) providing a non radioactive source for producing X-rays inside the flow passageway;
   (c) generating X-rays inside the flow passageway at a first intensity; and
   (d) passing the material in a flow through the flow passageway and the X-rays at a first rate sufficient to sterilize the material.

10. The method as in claim 9 further comprising:
    (e) cladding the flow passageway with a second material for containing X-rays.

11. The method as in claim 9 wherein step (b) further comprises providing an X-ray source having a vacuumated chamber containing a gas that produces an ECR plasma in an applied resonant magnetic field.

12. The method as in claim 9 wherein step (b) further comprises providing an ECR-X source.

13. The method as in claim 9 wherein step (b) further comprises providing more than one non radioactive X-ray source spaced apart, each source having a vacuumated chamber containing a gas that produces an ECR plasma in an applied resonant magnetic field and generating X-rays at an intensity so that the material flowing at a second rate is cumulatively exposed to X-rays sufficient to sterilize the material.

14. The method as in claim 13 wherein each non radioactive X-ray source is an ECR-X source.

15. The method as in claim 9 wherein steps (a) and (b) further comprise bending the flow passageway on opposite sides of the X-ray source and cladding the flow passageway between and about the bends with a material for containing X-rays so that X-rays generated by the source inside the flow passageway are confined within the flow passageway.

16. The method as in claims 11, 12, 13 or 14 wherein step (c) further comprises energizing each X-ray source with from 200 to 500 watts of microwave power.

* * * * *